United States Patent
Tanaka

(10) Patent No.: US 11,141,394 B2
(45) Date of Patent: Oct. 12, 2021

(54) CARBON DIOXIDE EXTERNAL PREPARATION

(71) Applicant: Masaya Tanaka, Ashiya (JP)

(72) Inventor: Masaya Tanaka, Ashiya (JP)

(*) Notice: Subject to any disclaimer, the term of this patent is extended or adjusted under 35 U.S.C. 154(b) by 0 days.

(21) Appl. No.: 16/639,498

(22) PCT Filed: Aug. 8, 2018

(86) PCT No.: PCT/JP2018/029812
§ 371 (c)(1),
(2) Date: Feb. 14, 2020

(87) PCT Pub. No.: WO2019/035405
PCT Pub. Date: Feb. 21, 2019

(65) Prior Publication Data
US 2021/0030702 A1    Feb. 4, 2021

(30) Foreign Application Priority Data
Aug. 17, 2017 (JP) .............................. JP2017-157598

(51) Int. Cl.
| | |
|---|---|
| *A61K 31/194* | (2006.01) |
| *A61K 8/02* | (2006.01) |
| *A61K 8/34* | (2006.01) |
| *A61K 8/362* | (2006.01) |
| *A61K 8/81* | (2006.01) |
| *A61K 9/00* | (2006.01) |
| *A61K 33/00* | (2006.01) |
| *A61K 47/10* | (2017.01) |
| *A61K 47/32* | (2006.01) |
| *A61Q 19/02* | (2006.01) |

(52) U.S. Cl.
CPC .......... *A61K 31/194* (2013.01); *A61K 8/0204* (2013.01); *A61K 8/34* (2013.01); *A61K 8/362* (2013.01); *A61K 8/8135* (2013.01); *A61K 9/0014* (2013.01); *A61K 33/00* (2013.01); *A61K 47/10* (2013.01); *A61K 47/32* (2013.01); *A61Q 19/02* (2013.01)

(58) Field of Classification Search
CPC ........... A61K 8/34; A61K 47/12; A61K 33/10
See application file for complete search history.

(56) References Cited

U.S. PATENT DOCUMENTS

| | | | | |
|---|---|---|---|---|
| 6,689,339 | B1* | 2/2004 | Tanaka | ................... A61P 17/10 424/44 |
| 7,879,359 | B2* | 2/2011 | Tanaka | ................... A61P 25/00 424/489 |
| 2004/0219230 | A1 | 11/2004 | Tanaka | |
| 2005/0175643 | A1 | 8/2005 | Tanaka | |
| 2006/0165607 | A1 | 7/2006 | Tanaka | |
| 2006/0257504 | A1 | 11/2006 | Tanaka et al. | |
| 2008/0213402 | A1 | 9/2008 | Tanaka et al. | |
| 2011/0165211 | A1 | 7/2011 | Tanaka | |

FOREIGN PATENT DOCUMENTS

| | | | |
|---|---|---|---|
| JP | 2000319187 A | * | 1/2000 |
| JP | 2000-319187 A | | 11/2000 |
| JP | 2001-302448 A | | 10/2001 |
| JP | 2005-89357 A | | 4/2005 |
| JP | 2005-194233 A | | 7/2005 |
| JP | 2014-193842 A | | 10/2014 |
| JP | 2014-224084 A | | 12/2014 |
| JP | 2015-34153 A | | 2/2015 |
| JP | 2015-180610 A | | 10/2015 |
| JP | 2017-43588 A | | 3/2017 |
| WO | WO 02/080941 A1 | | 10/2002 |
| WO | WO 03/057228 A1 | | 7/2003 |
| WO | WO 2004/004745 A1 | | 1/2004 |
| WO | WO 2005/016290 A1 | | 2/2005 |
| WO | WO 2006-080398 A1 | | 8/2006 |

OTHER PUBLICATIONS

Allison et al, Methods of Soil Analysis Part 2, 1965, summary (Year: 1965).*
Adeleke et al, South African Journal of Botany, vol. 108, 2017, pp. 393-406 (Year: 2017).*
Eichorst et al, Applied and Environmental Microbiology, 2012, pp. 2316-2327 (Year: 2012).*
Yu et al (Microbiology Open, 2016, vol. 5, pp. 604-615 (Year: 2016).*
Extension (Climate, Forests and Woodlands, Basic Soil Components, May 2019, https://climate-woodlands.extension.org/basic-soil-components/) (Year: 2019).*
JP-2000319187-A, Espacenet English translation, downloaded 2021 (Year: 2021).*
International Preliminary Report on Patentability and English translation of the Written Opinion of the International Searching Authority dated Oct. 30, 2018 for Application PCT/JP2018/029812.
International Search Report dated Oct. 30, 2018 for Application No. PCT/JP2018/029612.
International Preliminary Report on Patentability and English translation of the Written Opinion of the International Searching Authority dated Feb. 27, 2020 for Application No. PCT/JP2018/029812.
International Search Report dated Oct. 30, 2018 for Application No. PCT/JP2018/029812.
Extended European Search Report for European Application No. 18845570.3, dated Mar. 15, 2021.

* cited by examiner

*Primary Examiner* — Mark V Stevens
(74) *Attorney, Agent, or Firm* — Birch, Stewart, Kolasch & Birch, LLP

(57) ABSTRACT

Provided is a nonaqueous carbon dioxide external preparation in single dosage form, the external preparation comprising a paste base, carbonate, an acid and/or a substance which produces an acid by hydrolysis, and alcohol. Merely by being applied onto skin, this external preparation is useful due to obtaining the effect of a specific action of carbon dioxide.

4 Claims, No Drawings

CARBON DIOXIDE EXTERNAL PREPARATION

TECHNICAL FIELD

The present invention relates to a non-aqueous carbon dioxide external preparation that can be used just by being applied to the skin, or just by being supplied with additional water thereto.

BACKGROUND ART

Carbon dioxide external preparations are disclosed such as compositions for preparing external carbon dioxide agents consisting of an acid or a carbonate comprising viscous preparations or an acid or a carbonate comprising granules that generate carbon dioxide by the reaction of an acid and a carbonate when each viscous preparations or a viscous preparation and granules are mixed (patent documents 1-5);
a material for formation of carbon dioxide external preparation comprising a base agent that comprises a polymeric three-dimensional network structure impregnated with a viscous material containing at least an acid and water, and is made to contact with the skin in use, and a reactant that contains at least a carbonate, and is made to contact with the base agent at use so as to generate carbon dioxide (patent document 6);
carbon dioxide-supplying skin cosmetics consisting of (A) a non-aqueous liquid preparation comprising a carbonate or a bicarbonate and (B) acidic non-aqueous liquid preparation, wherein said preparation (A) and preparation (B) are mixed at use and further water is added thereto to generate carbon dioxide (patent document 7);
effervescent external preparations consisting of (A) an acidic non-aqueous liquid preparation and (B) a water-containing liquid preparation comprising a basic preparation, wherein said acidic non-aqueous liquid preparation (A) and said water-containing liquid preparation (B) are mixed and used (patent document 8); and
effervescent skin cosmetics of gelatinous or two-component type whose viscosity at 20° C. is more than 4000 mPa·s, which are practically non-aqueous (patent document 9).

PATENT DOCUMENTS

Patent document 1: JP 2000-319187A
Patent document 2: WO 2002/80941
Patent document 3: WO 2006/80398
Patent document 4: WO 2003/57228
Patent document 5: WO 2005/16290
Patent document 6: WO 2004/4745
Patent document 7: JP 2005-89357A
Patent document 8: JP 2015-180610A
Patent document 9: JP 2005-194233A

SUMMARY OF THE INVENTION

Problems to be Solved by the Invention

In carbon dioxide external preparations consisting of more than two components comprising viscous aqueous preparations, weight reduction and the like has been hard because a viscous aqueous preparation can contain only either one of an acid and a carbonate at the same time and the most weight of the preparation is occupied by water.

Furthermore, it has been troublesome to use carbon dioxide external preparations consisting of more than two components comprising viscous aqueous preparation because all the necessary components thereof must be mixed to generate carbon dioxide before use and the prepared carbon dioxide external preparation must be applied to the desired skin.

Weight of an effervescent skin cosmetic disclosed in patent document 9 is reduced as it is practically non-aqueous, but only two-component type carbon dioxide external preparations are disclosed in examples 1-10. Although skin cosmetics of mono-component type are disclosed in examples 11 and 12, physical properties of their gel have some troubles. No gelatinous skin cosmetics which were capable of evaluating physical property were obtained (see the Experimental Example 2 below).

Accordingly, an easily-used carbon dioxide external preparation of mono-component type that shows enough effects of carbon dioxide continuously by being supplied with water thereto has been desired.

Means for Solving Problems

The inventor has accomplished the present invention by the discovery that a pasty carbon dioxide external preparation comprising a paste base agent (hereinafter referred to "base agent" in some cases), an alcohol, a carbonate, an acid and/or a substance that generates an acid by hydrolysis (hereinafter referred to "alternative of acid" in some cases) as essential ingredients shows enough specific actions and effects of carbon dioxide such as vasodilation completely and continuously just by being applied to the skin or being supplied with water thereto.

Effect of the Invention

A carbon dioxide external preparation of the present invention can be applied to the skin or a cloth and the like because it is sticky. Actions and effects specific to carbon dioxide such as vasodilation, enhancement of muscle forth, acceleration of fatigue recovery, an anti-cancer effect by inducing cancer cell-specific apoptosis, acceleration of healing bone fracture, acceleration of wound healing, acceleration of fat metabolism, an effect of making beautiful skin and the like are obtained just by applying a carbon dioxide external preparation of the present invention to the skin or being supplied with additional water thereto. It is convenient to carry out and is easy to use.

Further, a carbon dioxide gas pack agent which is previously known can be provided by adding appropriate amount of water to a carbon dioxide external preparation of the present invention in a container to dissolve it so that it can be used for the above mentioned purposes.

MODE FOR CARRYING OUT THE INVENTION

A carbon dioxide external preparation of the present invention forms paste from a paste base agent, an alcohol, a carbonate, an acid and/or a substance that generates an acid by hydrolysis, and the said ingredients coexist stably without generating carbon dioxide till water is supplied thereto.

Although a carbon dioxide external preparation of the present invention usually contains no water, some water inclusion is allowable. The upper limit of water content in alcohol is about 2% though it depends on the ingredients. The upper limit of water content in a whole carbon dioxide external preparation is about 1.8%.

In the present invention, paste means fluid material that can be spread thinly and has enough viscosity and stickiness so that it does not drop off from the skin or the cloth where the paste is applied.

In the present invention, a paste base agent means a substance that gives viscosity to alcohol. Carboxyvinyl polymer is preferable as the paste base agent. Alkyl-modified carboxyvinyl polymer is considered as an equivalent of carboxyvinyl polymer in the present invention, and can be used as a substitute of carboxyvinyl polymer or with carboxyvinyl polymer.

Bicarbonate is considered as an equivalent of carbonate in the present invention, and can be used as a substitute of carbonate or with carbonate.

When water is supplied to a carbon dioxide external preparation of the present invention, a carbonate and an acid and/or a substance that generates an acid by hydrolysis are dissolved and react each other to generate carbon dioxide.

When the skin contains a proper amount of water, carbon dioxide is generated just by applying a carbon dioxide external preparation of the present invention to the skin because mainly alcohol of the said external preparation absorbs the skin water, which dissolves carbonate and acid and/or a substance that generates an acid by hydrolysis to react each other. Then, the generated carbon dioxide forms bubbles little and is absorbed through the skin immediately to show the actions. In case of poor amount of the skin water content or desiring to increase the amount of carbon dioxide generation, wetting the target skin before applying the preparation may be recommended. The wetting method is not limited. Dipping the target area into water, covering the target area with a wet towel or the like, applying steam or covering with polymer film may be recommended. Otherwise, spraying water or steam onto the surface of the said external preparation, or covering the said external preparation with a wet towel and the like to supply water thereto may be recommended. Further, covering the skin with polymer film to get wet the skin may be preferred. Of course, these methods may be combined properly.

Carboxyvinyl polymer is preferred as a paste base agent in the present invention. Any carboxyvinyl polymer that dissolves in alcohol and water may be used without limitation. Carboxyvinyl polymer is cited below as a concrete example of a paste base agent, but any substance that gives viscosity to alcohol can be used as a paste base agent in the present invention without limitation.

Blending amount of carboxyvinyl polymer in a carbon dioxide external preparation of the present invention may be one that gives appropriate viscosity and stickiness to the preparation so that the preparation forms paste and can be spread on the skin or the cloth and the like. Preferable blending amount of carboxyvinyl polymer is about 0.1-40 mass % of the whole amount of solid ingredients of a carbon dioxide external preparation of the present invention.

A thickener may further be added to a carbon dioxide external preparation of the present invention. In the present invention, a thickener means one other than carboxyvinyl polymer (hereinafter referred to "additional thickener" in some cases), and the relative blending amount of carboxyvinyl polymer is reduced by adding a thickener so that web drawing specific to carboxyvinyl polymer can be suppressed. Furthermore, it is preferable to add an additional thickener that has lower water-solubility or water-swelling rate compared to those of carboxyvinyl polymer because the water absorbing rate of the carbon dioxide external preparation becomes more slowly so that the dissolving rate of a carbonate and an acid and/or a substance that generates an acid by hydrolysis also become more slowly, and then the duration of carbon dioxide-generation is prolonged by the suppression of carbon dioxide generation rate.

As the additional thickener, one or more compounds selected from the group consisting of natural polymers, semi-synthetic polymers, synthetic polymers and inorganic compounds may be used.

As natural polymers, for example, plant-originated polymers such as arabic gum, carrageenan, galactan, agar, quince seed gum, guar gum, tamarind gum, tragacanth gum, pectin, mannan, locust bean gum, rice starch, flour starch, corn starch, and potato starch; microbial-originated polymers such as curdlan, xanthan gum, succinoglucan, dextran, hyaluronic acid, and pullulan; and protein polymers such as albumin, casein, collagen, gelatin and fibroin may be included.

As semi-synthetic polymers, cellulose polymers such as ethylcellulose, carboxymethylcellulose and its salts, carboxymethylethylcellulose and its salts, carboxymethyl starch and its salts, croscarmellose and its salts, crystallized cellulose, cellulose acetate, cellulose acetate phthalate, hydroxyethylcellulose, hydroxypropyl starch, hydroxypropylcellulose, hydroxypropylmethylcellulose, hydroxypropylmethylcellulose phthalate, powdered cellulose, methylcellulose, and methylhydroxypropylcellulose; starch polymers such as gelatinized (α-) starch, partially gelatinized (α-) starch, carboxymethyl starch, dextrin, and methyl starch; alginate polymers such as alginic acid, sodium alginate and propylene glycol alginate; and other polysaccharide polymers such as sodium chondroitin sulfate and sodium hyaluronate may be included.

As synthetic polymers, for example, sodium polyacrylate, polyvinylacetaldiethylaminoacetate, polyvinyl alcohol, polyvinyl pyrrolidone, methacrylic acid-ethyl acrylate copolymer, methacrylic acid—ethyl methacrylate copolymer, ethyl methacrylate.trimethylammoniumethyl chloride methacrylate copolymer and dimethylaminoethyl methacrylate-.methyl methacrylate copolymer may be included.

As inorganic compounds, for example, hydrated silicon dioxide, light anhydrous silica, colloidal alumina, bentonite, laponite and hectorite may be included.

Hydroxypropyl cellulose, hydroxypropyl methylcellulose, sodium carboxymethylcellulose, sodium polyacrylate, carrageenan, hydroxyethylcellulose, xanthan gum or gellan gum may be preferred as a thickener other than carboxyvinyl polymer.

Blending amount of an additional thickener is about 0.1-50 times the amount of carboxyvinyl polymer, and preferably about 5-20 times.

As an alcohol of a carbon dioxide external preparation of the present invention, any alcohol that is liquid at normal temperature may be used without limitations, and monohydric alcohol such as ethanol, methanol, n-propanol, isopropanol; polyhydric alcohol such as isopentyldiol, ethylene glycol, diethylene glycol, glycerin, diglycerin, 1,3-butylene glycol, 1,2-pentanediol, propanediol, propylene glycol, dipropylene glycol, hexylene glycol and polyethylene glycol may be included and one or more of these may be used. Among these, polyhydric alcohol is preferable.

Blending amount of an alcohol may be the one that gives appropriate viscosity and stickiness to a carbon dioxide external preparation of the present invention so that the preparation forms paste which can be spread on the skin or the cloth and the like, and at the same time has enough viscosity to prevent precipitation of alcohol-insoluble solid substances. Preferable blending amount of an alcohol is about 80-400 mass % of the whole solid substances of a carbon dioxide external preparation of the present invention.

When an alcohol-insoluble solid substance precipitated a little in a carbon dioxide external preparation of the present invention, the preparation can be used by stirring the said preparation by dispersing the precipitate widely before use.

Further, a particle size of alcohol-insoluble solid substances may preferably be as small as possible and specific gravity of each particle may preferably be the same or proximate to each other so as not to precipitate in a carbon dioxide external preparation of the present invention.

Alcohol is hygroscopic. When its water content is above certain content, carbon dioxide may be generated during the preparation process of a carbon dioxide external preparation of the present invention. Alcohol may preferably be used after being dried to avoid it. As a drying method, a known method using a desiccant such as molecular sieve, calcium oxide, magnesium oxide, anhydrous potassium carbonate, anhydrous sodium sulphate, anhydrous magnesium sulphate, silica, zeolite and the like may be used according to the type of alcohol.

Furthermore, a desiccant may further be added to a carbon dioxide external preparation of the present invention. As alcohol is hygroscopic, a carbon dioxide external preparation of the present invention may generate carbon dioxide before use because a carbonate and an acid and/or a substance that generates an acid by hydrolysis are dissolved by the water that is absorbed by the alcohol of the said external preparation. Consequently, carbon dioxide generation can be prevented by adding a desiccant to a carbon dioxide external preparation of the present invention till water is supplied thereto.

As a desiccant, a known desiccant that can be used according to the type of alcohol may be used. As the desiccant, for example, calcium oxide, magnesium oxide, anhydrous potassium carbonate, anhydrous sodium sulphate, anhydrous magnesium sulphate, silica, zeolite and the like may be included and one or more of these may be used.

Furthermore, anhydride of a carbonate or an acid and/or a substance that generates an acid by hydrolysis may be used as a desiccant. Of course, these may be used by appropriately combining with the above mentioned desiccant.

Any carbonate that reacts with an acid to generate carbon dioxide may be used in a carbon dioxide external preparation of the present invention without limitation. As the carbonate, for example, ammonium carbonate, ammonium bicarbonate, potassium carbonate, potassium bicarbonate, potassium sesquicarbonate, sodium carbonate, sodium bicarbonate, sodium sesquicarbonate, magnesium carbonate, magnesium bicarbonate, calcium bicarbonate and calcium carbonate may be included and one or more of these may be used.

Preferable blending amount of a carbonate is about 1-60 mass % of the whole solid substances of a carbon dioxide external preparation of the present invention.

A carbonate may be used in slow releasing granular material or the like prepared by common technologies to suppress the reaction rate with an acid.

As an acid of a carbon dioxide external preparation of the present invention, one or more acids selected from the group consisting of organic acids and inorganic acids that react with a carbonate to generate carbon dioxide may be used without limitation.

As an organic acid, for example, dicarboxylic acids such as oxalic acid, malonic acid, succinic acid, glutaric acid, adipic acid, pimelic acid, fumaric acid, maleic acid, phthalic acid, isophthalic acid, and terephthalic acid; acidic amino acids such as glutamic acid and aspartic acid; and hydroxy acids such as glycolic acid, malic acid, tartaric acid, itartaric acid, citric acid, isocitric acid, hydroxyacrylic acid, α-oxybutyric acid, glyceric acid, tartronic acid, salicylic acid, gallic acid, lactic acid, tropic acid, ascorbic acid and gluconic acid may be included and one or more of these may be used.

As an inorganic acid, for example, phosphoric acid, potassium dihydrogen phosphate, sodium dihydrogen phosphate, sodium sulfite, potassium sulfite, sodium pyrosulfite, potassium pyrosulfite, acidic sodium hexametaphosphate, acidic potassium hexametaphosphate, acidic sodium pyrophosphate, acidic potassium pyrophosphate and sulfamic acid may be included and one or more of these may be used.

Blending amount of an acid is the one that neutralizes a part of the carbonate of a carbon dioxide external preparation of the present invention, and preferably the one that neutralizes all of the carbonate.

A solid acid may be used in slow releasing granular material or the like prepared by common technologies to suppress the reaction rate with a carbonate.

As a substance that generates an acid by hydrolysis used in a carbon dioxide external preparation of the present invention, for example, lactones such as glucono-delta-lactone and pantolactone; cyclic dimers of organic acid such as D,L- or L-lactide (3,6-dimethyl-1,4-dioxane-2,5-dione) and D,L- or L-glycolide; acid anhydrides such as phthalic anhydride, maleic anhydride, and succinic anhydride may be included and one or more of these may be used.

When a substance that generates an acid by hydrolysis is used as an acid in a carbon dioxide external preparation of the present invention, the initial amount of carbon dioxide generation may be smaller compared to a carbon dioxide external preparation that contains only an acid because an amount of an acid generated by being dissolved and hydrolyzed is small at first. Combining an acid with this, the amount of carbon dioxide generated at initial water supply becomes beyond a certain level and also the duration of carbon dioxide-generation may be prolonged.

Blending amount of a substance that generates an acid by hydrolysis is the one that neutralizes a part of the carbonate of a carbon dioxide external preparation of the present invention, and preferably the one that neutralizes all of the carbonate.

A substance that generates an acid by hydrolysis may be used in slow releasing granular material or the like prepared by common technologies to suppress the reaction rate with a carbonate.

Further, a water-soluble excipient may be added to a carbon dioxide external preparation of the present invention. Carbon dioxide is generated by the reaction of a carbonate and an acid in the present invention. This reaction needs water. If a water-soluble excipient is contained in a carbon dioxide external preparation of the present invention, the water amount absorbed by the said preparation is increased so that the carbon dioxide-generating reaction is increased and also the amount of carbon dioxide generated is increased.

As a water-soluble excipient, an excipient whose solubility is "freely soluble" or "very soluble" according to the Japanese Pharmacopoeia 15th edition is preferable. As concrete examples, monosaccharides such as arabinose, galactose, glucose, xylose, sorbose, fructose, mannose, ribose and rhamnose, or disaccharides such as sucrose, cellobiose, trehalose, maltose, lactulose and lactose, or sugar alcohols such as arabitol, erythritol, xylitol, sorbitol, maltitol and mannitol may be included and one or more of these may be used.

Further, an exothermic agent may be added to a carbon dioxide external preparation of the present invention. In the present invention, carbon dioxide is generated by the reaction of a carbonate and an acid in the presence of water. As this is an endothermal reaction, blood flow-increasing action of transdermally absorbed carbon dioxide may be interrupted by the low temperature of the carbon dioxide external preparation that lowers the skin temperature when the preparation is applied to the skin. An exothermic agent can improve this problem.

As an exothermic agent, a substance that generates hydration heat when it dissolves in water, for example, such as calcium chloride may be used. Blending amount of an exothermic agent can be easily determined by the amount of water to be supplied to a carbon dioxide external preparation of the present invention at use, heating value per weight of an exothermic agent and the desired water temperature. For example, if the supplying water amount to a carbon dioxide external preparation of the present invention is 5 g, theoretically 123 mg of calcium chloride, when calcium chloride is used as an exothermic agent, may be blended thereto to raise the water temperature 5° C. Blending amount of an exothermic agent may be selected appropriately. Blending amount is preferably 5-30 mass % of the whole solid substances of a carbon dioxide external preparation of the present invention.

When a carbon dioxide external preparation of the present invention is dissolved in or swelled with an appropriate amount of water, it generates carbon dioxide and gives a viscous carbon dioxide external preparation. Too much water is not preferable because it gives a viscous liquid with a low viscosity so that carbon dioxide leaking increases. Blending ratio of water to a carbon dioxide external preparation of the present invention is about 0.1-40 mass part, and preferably 0.5-10 mass part.

When a carbon dioxide external preparation of the present invention is applied directly to the wet wound surface, no additional water is necessary because the exudate or the like from the wound surface supplies water to the said preparation. Also in an oral cavity or a large bowel, no additional water is necessary when a carbon dioxide external preparation of the present invention is applied directly thereto. Of course, additional water supply in such usage may increase carbon dioxide generation amount.

A preferable mode of a carbon dioxide external preparation of the present invention is the one that comprises carboxyvinyl polymer as a paste base agent, malic acid and/or tartalic acid and sodium dihydrogen phosphate as an acid, one or more of dihydric alcohol or trihydric alcohol selected from the group of 1,3-butylene glycol, propylene glycol and glycerin, one or more of additional thickeners selected from the group of hydroxypropyl cellulose, hydroxypropyl methylcellulose, carrageenan, sodium alginate and sodium carboxymethylcellulose and sodium sulphate as an optional desiccant.

A carbon dioxide external preparation of the present invention may be used as a sheet preparation by being spread on a supporting material. If the supporting material is water-retentive, it is better to supply water to the said sheet than using it only by applying to the objective area because carbon dioxide generating amount is increased.

As a water-retentive supporting material, woven fabric, nonwoven fabric and sponge may be included and one or more of these may be used.

Prevention and treatment of hemorrhoid and also treatment of constipation that was caused by the lowering of the reflection function of the defection may be done by infusion of a carbon dioxide external preparation of the present invention into the large bowel because the preparation absorbs water in the bowel and generates carbon dioxide.

EXAMPLES

The present invention is explained concretely below by examples, but the present invention is not limited to these examples.

Examples 1-74

As shown in the tables 1-6, carbon dioxide external preparations of the present invention were prepared from a carbonate, an acid and/or a substance that generates an acid by hydrolysis, an alcohol, carboxyvinyl polymer (base agent), optionally a thickener other than carboxyvinyl polymer (additional thickener), a water-soluble thickener and a desiccant according to a routine procedure. Values in the tables show mass parts of the substances. As an alcohol, reagents were used as they were if no specific comment was added. Blending amount of an alcohol that was used after drying is described in italic type.

Drying of 1,3-butylene glycol and propylene glycol was done by stirring over anhydrous sodium sulphate in a transparent or semitransparent container such as a plastic bottle or the like with a cap. Anhydrous sodium sulphate coagulates in the bottom of the container when it absorbs water of polyhydric alcohol. Anhydrous sodium sulphate was added till the further added anhydrous sodium sulphate did not coagulate and precipitated in granular state. After that, the container was covered with the cap and left overnight. The alcohol was used after being confirmed that the sodium sulphate stayed in the fine granular state in the bottom of the container.

Drying of glycerin was done by using silicon dioxide instead of anhydrous sodium sulphate. Silicon dioxide was added to glycerin about 5% of the mass of glycerin in a transparent or semitransparent container such as a plastic bottle or the like with a cap and then the bottle was shaken. Then, the bottle was covered with the cap, left overnight and was used from the next day.

As ethanol, anhydrous ethanol was used.

TABLE 1

| | Example | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
|---|---|---|---|---|---|---|---|---|---|---|---|---|---|---|---|---|---|---|---|---|---|---|---|
| Carbonate | Sodium bicarbonate | 2 | 2 | 2 | 2 | 2 | 2 | 2 | 2 | 2 | 4 | | | 20 | | 20 | 20 | 20 | 25 | 20 | 15 | 4 | 15 |
| | Sodium carbonate | | | | | | | | | | | 4 | 20 | | | | | | | | | | |
| | Calcium carbonate | | | | | | | | | | | | | | 20 | | | | | | | | |
| Acid or alternative of acid | Malic acid | | 2 | 2 | 2 | 2 | 2 | 1 | | | | 3 | 15 | 15 | | 15 | 15 | 15 | 20 | 15 | 8 | 4 | 5 |
| | Citric acid | | | | | | | | 1.5 | 1.5 | 3 | | | | | | | | | | | | |
| | Sodium dihydrogen phosphate | | | | | | | | | | | | | | | | | | | | | | |
| | Glucono delta lactone | 2 | | | | | | | | | | | | | | | | | 40 | | | | |

TABLE 1-continued

| | Example | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
|---|---|---|---|---|---|---|---|---|---|---|---|---|---|---|---|---|---|---|---|---|---|---|---|
| Alcohol | 1,3-butylene glycol | 12 | 18 | 24 | 18 | 12 | | | 20 | 20 | 30 | 30 | | 200 | 250 | 250 | 200 | 200 | | 100 | 100 | | 100 |
| | Glycerin | | | | | | 50 | 50 | | | | | | | | | | | 250 | | | | |
| | 1,2-propanediol | | | | | | | | | | | | 150 | | | | | | | | | | |
| | Ethanol | | | | | | | | | | | | | | | | | | | | 20 | | |
| Base agent | Carboxyvinyl polymer | 1 | 1 | 1 | 1 | 1 | 2 | 1 | 1 | 1 | 1 | 1 | 2 | 1 | 1 | 1 | 1 | 1 | 1 | 1 | 1 | 1 | 1 |
| Additional thickener | Carrageenan | | | | | | | | | 5 | | | | | | | | | | | | | |
| | Xanthan gum | | | | | | | | | 5 | | | | | | | | | | | | | |
| | Gellan gum | | | | | | | | | | | 10 | | | | | | | | | | | |
| | Sodium alginate | 5 | 5 | 5 | | 5 | | | | | | | | 100 | 100 | 100 | 100 | 100 | 100 | | | | |
| | Sodium carboxymethylcellulose | | | | 5 | | | | | | | | | | | | | | | | | | |
| Water-soluble excipient | Lactose | 5 | 5 | | | | | | | | | | | | | | | | | | | | |
| | Glucose | | | | | | 5 | | | | | | | | | | | | | | | | |
| | Trehalose | | | 5 | | | | | | | | | | | | | | | | | | | |
| Desiccant | Sosdium sulphate | | | | | | | | | | | | | 8 | | | | | | 3 | 2 | | 2 |
| | Silicon dioxide | | | | | | | | | | | | | | | | 8 | | 8 | | | | |

TABLE 2

| | Example | 23 | 24 | 25 | 26 | 27 | 28 | 29 | 30 | 31 | 32 | 33 |
|---|---|---|---|---|---|---|---|---|---|---|---|---|
| Carbonate | Sodium bicarbonate | 90 | 9 | 90 | 90 | 90 | 90 | 90 | 90 | 90 | 90 | 90 |
| | Sodium carbonate | | | | | | | | | | | |
| | Calcium carbonate | | | | | | | | | | | |
| Acid or alternative of acid | Malic acid | 20 | 1 | 10 | 40 | 30 | 10 | 10 | 10 | 10 | 10 | 10 |
| | Tartaric acid | | | | | | | | | | | |
| | Sodium dihydrogen phosphate | | | | | | | | | | | |
| | Glucono delta lactone | | | 10 | 80 | | 80 | 60 | 60 | 60 | 60 | 60 |
| Alcohol | 1,3-butylene glycol | 600 | 60 | 600 | 600 | 600 | 600 | 600 | 600 | 600 | 600 | 600 |
| | Glycerin | | | | | | | | | | | |
| | 1,2-propanediol | | | | | | | | | | | |
| | 1,2-pentanediol | | | | | | | | | | | |
| Base agent | Carboxyvinyl polymer | 6 | 2 | 6 | 6 | 6 | 6 | 6 | 4 | 2 | 4 | 4 |
| Additional thickener | Polyvinyl pyrrolidone | | | | | | | | | | | |
| | Hydroxypropylcellulose | 114 | | | 114 | 114 | 114 | 114 | 40 | 40 | 116 | 36 |
| | Hydroxypropylmethylcellulose | | | | | | | | | | 118 | 80 |
| | Sodium alginate | | | | | | | | | | | |
| | Sodium carboxymethylcellulose | | | | | | | | | | | |
| | Polyvinyl alcohol | | | | | | | | | | | |
| | Carrageenan | | | | | | | | 74 | 76 | | |
| Water-soluble excipient | Lactose | | | 10 | | | | | | | | |
| Desiccant | Sosdium sulphate | 12 | 1.2 | | | | | | 20 | 12 | 60 | 12 |
| | Silicon dioxide | | | | | | | | | | | |
| | Silica gel | | | 12 | 12 | 12 | 12 | 12 | | | | |

TABLE 3

| | Example | 34 | 35 | 36 | 37 | 38 | 39 | 40 | 41 | 42 | 43 | 44 |
|---|---|---|---|---|---|---|---|---|---|---|---|---|
| Carbonate | Sodium bicarbonate | 90 | 90 | 150 | 50 | 30 | 30 | 30 | 19 | 90 | 30 | 140 |
| | Sodium carbonate | | | | | | | | | | | |
| | Calcium carbonate | | | | | | | | | | | |
| Acid or alternative of acid | Malic acid | 10 | 10 | 15 | 6 | 3 | | | | | | |
| | Tartaric acid | | | | | | | | | 10 | | |
| | Sodium dihydrogen phosphate | | | | | | 10 | 10 | 10 | | 10 | |
| | Glucono delta lactone | 60 | 60 | 100 | 40 | 20 | 20 | 20 | 20 | 60 | 20 | 160 |
| Alcohol | 1,3-butylene glycol | | 100 | 1000 | | 600 | 600 | 600 | 600 | 600 | 200 | 1000 |
| | Glycerin | | | | | | | | | | | |
| | 1,2-propanediol | 600 | 500 | | 2500 | | | | | | | |
| | 1,2-pentanediol | | | | | | | | | | | |
| Base agent | Carboxyvinyl polymer | 4 | 4 | 7 | 20 | 4 | 4 | 4 | 4 | 4 | 1 | 3 |
| Additional thickener | Polyvinyl pyrrolidone | | | | | | | | | | | |
| | Hydroxypropylcellulose | 36 | 36 | 60 | 180 | 36 | 36 | 36 | 36 | 40 | | 40 |
| | Hydroxypropylmethylcellulose | 80 | 80 | 125 | 400 | 80 | 80 | 80 | 80 | | 40 | 80 |
| | Sodium alginate | | | | | | | | | | | |
| | Sodium carboxymethylcellulose | | | | | | | | | | | |
| | Polyvinyl alcohol | | | | | | | | | | | |

TABLE 3-continued

|  | Example | 34 | 35 | 36 | 37 | 38 | 39 | 40 | 41 | 42 | 43 | 44 |
|---|---|---|---|---|---|---|---|---|---|---|---|---|
| Water-soluble excipient | Carrageenan<br>Lactose |  |  |  |  |  |  |  |  | 40 |  |  |
| Desiccant | Sosdium sulphate<br>Silicon dioxide<br>Silica gel | 40 | 40 | 7 | 3 | 40 | 40 | 20 | 20 | 20 | 10 | 40 |

TABLE 4

|  | Example | 45 | 46 | 47 | 48 | 49 | 50 | 51 | 52 | 53 | 54 | 55 |
|---|---|---|---|---|---|---|---|---|---|---|---|---|
| Carbonate | Sodium bicarbonate | 20 | 90 | 60 | 28 | 150 | 14 | 280 | 20 | 140 | 40 | 90 |
|  | Sodium carbonate |  |  |  |  |  |  |  |  |  |  |  |
|  | Calcium carbonate |  |  |  |  |  |  |  |  |  |  |  |
| Acid or alternative of acid | Malic acid | 1 |  | 1 | 2.8 | 8 | 1.6 | 28 | 7 | 14 |  |  |
|  | Tartaric acid |  |  |  |  |  |  |  |  |  |  |  |
|  | Sodium dihydrogen phosphate |  | 4 |  |  |  |  |  |  |  | 10 | 9 |
|  | Glucono delta lactone | 20 | 60 | 60 | 18 | 160 | 9 | 180 | 20 | 90 | 60 | 60 |
| Alcohol | 1,3-butylene glycol | 600 | 600 | 600 | 180 |  | 180 | 1800 | 200 | 1800 | 600 | 810 |
|  | Glycerin |  |  |  |  | 1000 |  |  |  |  |  |  |
|  | 1,2-propanediol |  |  |  |  |  |  |  |  |  |  |  |
|  | 1,2-pentanediol |  |  |  |  |  |  |  |  |  |  |  |
| Base agent | Carboxyvinyl polymer | 3 | 3 | 3 | 9 | 3 | 1 | 9 | 1 | 9 | 3 | 3 |
| Additional thickener | Polyvinyl pyrrolidone |  |  |  |  |  |  |  |  |  |  |  |
|  | Hydroxypropylcellulose | 40 | 20 | 40 | 12 | 40 | 12 | 200 | 13 | 120 | 40 | 40 |
|  | Hydroxypropylmethylcellulose | 70 | 80 | 80 | 24 | 80 | 24 | 400 | 26 | 240 | 80 | 80 |
|  | Sodium alginate |  |  |  |  |  |  |  |  |  |  |  |
|  | Sodium carboxymethylcellulose |  |  |  |  |  |  |  |  |  |  |  |
|  | Polyvinyl alcohol |  |  |  |  |  |  |  |  |  |  |  |
|  | Carrageenan |  |  |  |  |  |  |  |  |  |  |  |
| Water-soluble excipient | Lactose |  |  |  |  |  |  |  |  |  |  |  |
| Desiccant | Sosdium sulphate | 20 | 20 | 20 | 6 |  | 4 | 60 | 7 | 120 | 10 | 20 |
|  | Silicon dioxide |  |  |  |  |  |  |  |  |  |  | 40 |
|  | Silica gel |  |  |  |  |  |  |  |  |  |  |  |

TABLE 5

|  | Example | 56 | 57 | 58 | 59 | 60 | 61 | 62 | 63 | 64 | 65 | 66 |
|---|---|---|---|---|---|---|---|---|---|---|---|---|
| Carbonate | Sodium bicarbonate | 15 | 15 | 15 | 22 | 22 | 22 | 22 | 28 | 28 | 28 | 4 |
|  | Sodium carbonate |  |  |  |  |  |  |  |  |  |  |  |
|  | Calcium carbonate |  |  |  |  |  |  |  |  |  |  |  |
| Acid or alternative of acid | Malic acid |  |  |  |  | 2 | 4 | 4 | 6 | 6 | 4 | 3 |
|  | Tartaric acid |  |  |  |  |  |  |  |  |  |  |  |
|  | Sodium dihydrogen phosphate | 17 | 20 | 20 | 30 | 25 | 25 | 25 | 31 | 31 | 31 | 10 |
|  | Glucono delta lactone |  |  |  |  |  |  |  |  |  |  |  |
| Alcohol | 1,3-butylene glycol | 200 | 300 | 300 |  | 300 | 300 |  | 375 | 375 | 375 | 60 |
|  | Glycerin |  |  |  |  |  |  |  |  |  |  |  |
|  | 1,2-propanediol |  |  |  |  |  |  | 300 |  |  |  |  |
|  | 1,2-pentanediol |  |  |  | 300 |  |  |  |  |  |  |  |
| Base agent | Carboxyvinyl polymer | 1 | 1 | 4 |  | 1 | 1 | 1 | 1 | 1 | 1 | 2 |
| Additional thickener | Polyvinyl pyrrolidone |  |  |  |  |  |  |  |  |  |  |  |
|  | Hydroxypropylcellulose | 13 | 13 | 10 | 10 | 10 | 10 | 10 | 10 | 10 | 10 |  |
|  | Hydroxypropylmethylcellulose | 26 | 26 |  |  |  |  |  |  |  |  |  |
|  | Sodium alginate |  |  | 30 |  |  |  |  |  |  |  |  |
|  | Sodium carboxymethylcellulose |  |  |  | 30 | 30 | 30 | 30 | 30 | 30 | 30 |  |
|  | Polyvinyl alcohol |  |  |  |  |  |  |  |  |  |  |  |
|  | Carrageenan |  |  |  |  |  |  |  |  |  |  |  |
| Water-soluble excipient | Lactose |  |  |  |  |  |  |  |  |  |  |  |
| Desiccant | Sosdium sulphate | 16 | 25 | 25 | 25 | 12 | 12 | 12 | 10 |  |  |  |
|  | Silicon dioxide |  |  |  |  |  |  |  |  |  |  |  |
|  | Silica gel |  |  |  |  |  |  |  |  |  |  |  |

TABLE 6

| | Example | 67 | 68 | 69 | 70 | 71 | 72 | 73 | 74 |
|---|---|---|---|---|---|---|---|---|---|
| Carbonate | Sodium bicarbonate | 4 | 90 | 90 | 90 | 90 | 30 | 50 | 60 |
| | Sodium carbonate | | | | | | | | |
| | Calcium carbonate | | | | | | | | |
| Acid or alternative of acid | Malic acid | 5 | 40 | 30 | 10 | 10 | 40 | 50 | 60 |
| | Tartaric acid | | | | | | | | |
| | Sodium dihydrogen phosphate | 20 | | | | | 50 | 60 | 40 |
| | Glucono delta lactone | | | | 80 | 60 | | | |
| Alcohol | 1,3-butylene glycol | 60 | 600 | 600 | 600 | 600 | 600 | 600 | 600 |
| | Glycerin | | | | | | | | |
| | 1,2-propanediol | | | | | | | | |
| | 1,2-pentanediol | | | | | | | | |
| Base agent | Carboxyvinyl polymer | 2 | 6 | 6 | 6 | 6 | | 6 | |
| | Alkyl-modified carboxyvinyl polymer | | | | | | 30 | 20 | 25 |
| Additional thickener | Hydroxypropylcellulose | | 114 | 114 | 114 | 40 | | | |
| | Hydroxypropylmethylcellulose | | | | | | | | |
| | Sodium alginate | | | | | | | | |
| | Sodium carboxymethylcellulose | | | | | | | | |
| | Polyvinyl alcohol | | | | | | | | |
| | Carrageenan | | | | | | 74 | | |
| Desiccant | Sosdium sulphate | | | | | | | | |
| | Silicon dioxide | | | | | | | | |
| | Silica gel | | 12 | 12 | 12 | 12 | | | |
| Exothermic agent | Calcium chloride | | 90 | 40 | 40 | 40 | | | |

Test Example 1 Physical Property Evaluation

1) Viscosity

Viscosity of a carbon dioxide external preparation of the present invention that was prepared in a glass bottle was evaluated 30 minutes after preparation by tilting the glass. A preparation that flowed out of the glass immediately after tilting the glass was evaluated as ×, a preparation that flowed down slowly like honey was evaluated as Δ, and a preparation that did not flow down within 30 seconds was evaluated as ○.

2) Storage Stability

For some examples, about 1 g of a carbon dioxide external preparation of the present invention was stored at 40° C. in an aluminum pouch having 115 mm×90 mm size that was heat-sealed after the least possible deaeration of the pouch. After 4 weeks, the aluminum pouch of the example was visually observed.

The evaluation results are shown in tables 8-9. All of the carbon dioxide external preparations of the present invention tested showed good viscosity and also good storage stability.

Test Example 2 Comparison to Prior Art

According to example 11 of the patent document 9, an effervescent skin cosmetic was prepared in 50 ml glass beaker from 1.5 g of sodium bicarbonate, 50 mg of phenoxyethanol, 1.5 g of anhydrous citric acid, 100 mg of hydroxypropylmethylcellulose and 6.85 g of 1,3-butylene glycol. An effervescent skin cosmetic was prepared 3 times in total from hydroxypropylmethylcellulose of different production lots, but all the obtained effervescent skin cosmetics showed poor viscosity so that solid substances precipitated in the bottom of the beaker. Evaluation for a shower cosmetic was tried by 62-years old male by applying 1.5 g of the effervescent skin cosmetic on the back of the left hand, but evaluation was hard because all the effervescent skin cosmetics flowed down immediately.

Test Example 3 Vasodilator Action

1) Intensity and Persistance of Skin Redness

The main basis of the efficacy of a carbon dioxide external preparation exists in the vasodilator action caused by the transdermal absorption of carbon dioxide (Tanaka, Masaya, Carbon dioxide external preparation "eCO2 GEL", monthly BIO-INDUSTRY, November 74-83, 2006, CMC Publishing CO., LTD). Therefore, the intensity of vasodilator action is proportional to the intensity of the skin redness in the same subject. So the intensity of redness caused by the examples were evaluated comparing with those of a carbon dioxide pack agent eCO2 GEL B.C. (product of Cosmepro company) by visual observation.

TABLE 7

EVALUATION CRITERIA FOR CARBON DIOXIDE EXTERNAL PREPARATION

| | |
|---|---|
| Intensity of skin redness 1 minute after application | 3 (Stronger than the compared sample) |
| | 2 (Same as the compared sample) |
| | 1 (Weaker than the compared sample) |
| | 0 (No skin redness) |
| Persistence of skin redness | 3 (Redness continues for more than 20 minutes) |
| | 2 (Redness continues for 10-20 minutes) |
| | 1 (Redness continues for 5-10 minutes) |
| | 0 (Redness continues less than 5 minutes) |

Specifically, 0.2 g of a carbon dioxide external preparation of the present invention was applied on the back of the left hand of a human subject (62-years old male) in 4 cm square, then a piece of 4 cm-square cut cotton containing about 2 g of purified water was put over the applied preparation immediately. Redness of the skin under the said preparation and its persistence were evaluated according to the criteria below by a tester by visual observation. Carbon dioxide pack agent was prepared by using eCO2 GEL B.C. (product of Cosmepro company), and 1 g of the agent was applied in 4 cm square on the back of the right hand for comparison.

2) Measurement of pH

It is known that the lower the pH of water is, the more carbon dioxide exists in molecular state (non-dissociated carbonic acid) in water, so that the amount of the transdermally absorbed carbon dioxide increases (refer to the aforementioned monthly BIO-INDUSTRY). Then, the pH was measured by applying pH test paper to a piece of cut cotton that is adhered to a carbon dioxide external preparation of the present invention 2 minutes after application of the preparation.

The test results are shown in tables 8-9 with the result of the physical properties evaluation. Carbon dioxide external preparations of the present invention mostly showed acidic pH values, and the intensity and persistence of redness showed good results.

TABLE 8

| | | 1 | 2 | 3 | 4 | 5 | 6 | 7 | 8 | 9 | 10 | 11 | 12 |
|---|---|---|---|---|---|---|---|---|---|---|---|---|---|
| Evaluation | pH | 5.0 | 4.0 | 3.5 | 3.5 | 3.5 | 3.5 | 4.5 | 3.5 | 3.5 | 3.5 | 3.5 | 3.5 |
| | Intensity of redness | 3 | 3 | 3 | 3 | 3 | 3 | 3 | 3 | 3 | 3 | 3 | 3 |
| | Persistence of redness | 1 | 3 | 3 | 3 | 3 | 3 | 2 | 3 | 3 | 3 | 3 | 3 |
| | Viscosity | ○ | ○ | ○ | ○ | ○ | ○ | ○ | ○ | ○ | ○ | ○ | ○ |
| | Storage stability at 40° C. | | | | | | | | | | | | |

| | | 13 | 14 | 15 | 16 | 17 | 18 | 19 | 20 | 21 | 22 | 23 | 24 |
|---|---|---|---|---|---|---|---|---|---|---|---|---|---|
| Evaluation | pH | 4.0 | 7.0 | 4.0 | 4.5 | 4.5 | 4.5 | 4.5 | 4.5 | 3.5 | 4.5 | 4 | 4.5 |
| | Intensity of redness | 3 | 1 | 3 | 3 | 3 | 3 | 3 | 3 | 3 | 3 | 2 | 2 |
| | Persistence of redness | 2 | 1 | 3 | 3 | 3 | 3 | 3 | 2 | 3 | 2 | 3 | 3 |
| | Viscosity | ○ | ○ | △ | ○ | ○ | △ | ○ | ○ | △ | ○ | ○ | ○ |
| | Storage stability at 40° C. | | | | ○ | ○ | | ○ | ○ | | ○ | ○ | |

| | | 25 | 26 | 27 | 28 | 29 | 30 | 31 | 32 | 33 | 34 | 35 | 36 |
|---|---|---|---|---|---|---|---|---|---|---|---|---|---|
| Evaluation | pH | 4.5 | 3.5 | 4.5 | 3 | 4.5 | 4 | 4.5 | 4.5 | 4.5 | 4.5 | 4.5 | 4.5 |
| | Intensity of redness | 2 | 3 | 3 | 2 | 1 | 3 | 3 | 3 | 3 | 3 | 3 | 3 |
| | Persistence of redness | 3 | 3 | 3 | 3 | 3 | 3 | 3 | 3 | 3 | 3 | 3 | 3 |
| | Viscosity | ○ | ○ | ○ | ○ | △ | △ | △ | ○ | △ | △ | △ | △ |
| | Storage stability at 40° C. | ○ | ○ | | | | | | | ○ | | ○ | ○ |

| | | 37 | 38 | 39 | 40 | 41 | 42 | 43 | 44 | 45 | 46 | 47 | 48 |
|---|---|---|---|---|---|---|---|---|---|---|---|---|---|
| Evaluation | pH | 4.5 | 4.5 | 4.5 | 4.5 | 4.5 | 4.5 | 4.5 | 4.5 | 4.5 | 4.5 | 4.5 | 4.5 |
| | Intensity of redness | 2 | 3 | 3 | 3 | 3 | 3 | 3 | 3 | 3 | 3 | 3 | 3 |
| | Persistence of redness | 3 | 3 | 3 | 3 | 3 | 3 | 3 | 3 | 3 | 3 | 3 | 3 |
| | Viscosity | ○ | ○ | ○ | ○ | ○ | △ | △ | △ | △ | △ | ○ | ○ |
| | Storage stability at 40° C. | | | | | | | | | | | | |

TABLE 9

| | | 49 | 50 | 51 | 52 | 53 | 54 | 55 | 56 | 57 | 58 | 59 | 60 |
|---|---|---|---|---|---|---|---|---|---|---|---|---|---|
| Evaluation | pH | 4.5 | 4.5 | 4.5 | 4.5 | 4.5 | 4.5 | 4.5 | 4.5 | 4.5 | 4.5 | 4.5 | 4.5 |
| | Intensity of redness | 3 | 2 | 3 | 2 | 3 | 3 | 3 | 2 | 2 | 3 | 2 | 1 |
| | Persistence of redness | 3 | 3 | 3 | | 3 | 3 | 3 | 3 | 3 | 3 | 3 | 3 |
| | Viscosity | △ | ○ | ○ | ○ | ○ | ○ | ○ | ○ | △ | △ | △ | △ |
| | Storage stability at 40° C. | | | | | | | | | | | | |

| | | 61 | 62 | 63 | 64 | 65 | 66 | 67 | 68 | 69 | 70 | 71 | 72 |
|---|---|---|---|---|---|---|---|---|---|---|---|---|---|
| Evaluation | pH | 4.5 | 4 | 4.5 | 4.5 | 4.5 | 4 | 4 | 3.5 | 4.5 | 3 | 4.5 | 4.5 |
| | Intensity of redness | 3 | 3 | 2 | 3 | 3 | 2 | 2 | 3 | 3 | 2 | 1 | 3 |
| | Persistence of redness | 3 | 3 | 3 | 3 | 3 | 3 | 3 | 3 | 3 | 3 | 3 | 3 |
| | Viscosity | △ | △ | △ | △ | △ | △ | ○ | ○ | ○ | ○ | △ | ○ |
| | Storage stability at 40° C. | ○ | | | ○ | | ○ | | ○ | | | | ○ |

| | | 73 | 74 |
|---|---|---|---|
| Evaluation | pH | 4.5 | 4.5 |
| | Intensity of redness | 3 | 3 |
| | Persistence of redness | 3 | 3 |
| | Viscosity | ○ | ○ |
| | Storage stability at 40° C. | ○ | ○ |

Test Example 4 Muscle Fatigue Recovery Test

Effects on muscle training and recovery of muscle fatigue by transdermally absorbed carbon dioxide are known (The Journal of the Japanese Orthopaedic Association, 88:34-39, 2014). In test example 4, recovery of grip strength fall caused by muscle fatigue was tested using a carbon dioxide external preparation of the present invention. This test was conducted by an orthopaedic doctor in an orthopaedic clinic.

First, grip strength of both hands of 6 male subjects was measured by a digital grip dynamometer. In general, grip strength is smoothly exerted in the dominant hand. Accordingly, a carbon dioxide external preparation was applied to the non-dominant hand to measure the effect of a carbon dioxide external preparation of the present invention more precisely.

To the whole of the non-dominant forearm, 1 g of the carbon dioxide external preparation of example 65 was applied. Grip strength of both hands was measured after 10 minutes rest. The first measurement of grip strength causes muscle fatigue. So, when the grip strength is measured 10 minutes after the first measurement, the grip strength usually decreases. The grip strength of the non-dominant hand to which a carbon dioxide external preparation of the present invention is applied may be expected to decrease a little or even increase than the dominant hand to which a carbon dioxide external preparation of the present invention is not applied if the muscle fatigue is recovered or the muscle strength is increased by a carbon dioxide external preparation of the present invention.

For example, when the grip strength of the dominant hand decreases 1 kg by muscle fatigue, its change is −1 kg. If the grip strength change of the non-dominant hand to which a carbon dioxide external preparation of the present invention is applied is +1 kg, the muscle fatigue recovery degree may be estimated as +2 kg because the carbon dioxide external preparation of the present invention changes −1 kg of the grip strength change into +1 kg of the grip strength change in the same subject on the assumption that the muscle fatigue recovery power of both hands are the same. Accordingly, the grip strength recovery was defined as follows.

(Grip strength change of the non-dominant hand)−
(Grip strength change of the dominant hand)=
Recovered grip strength by the carbon dioxide
external preparation  [Numerical expression 1]

In this test, +0.5 kg or more of recovered grip strength by a carbon dioxide external preparation of the present invention was evaluated effective, and less than +0.5 kg of the one was evaluated ineffective. The results are shown in table 10.

It is clear from Table 10 that the grip strength of the dominant hand of all subjects decreased or hardly changed at the grip strength measurement 10 minutes after the first measurement by the muscle fatigue of the first measurement. On the other hand, muscle fatigue recovery effect of a carbon dioxide external preparation of the present invention was obvious because the grip strength decrease of the non-dominant hand was very little or contrarily the grip strength increased.

TABLE 10

| Subject age (non-dominant hand) | Right hand grip strength (kg) | | | Left hand grip strength (kg) | | | Recovered grip strength (kg) |
|---|---|---|---|---|---|---|---|
| | Before | 10 min. After | Change | Before | 10 min. After | Change | |
| 50 years (left) | 44.9 | 39.3 | −5.6 | 39.6 | 42.6 | +3.0 | +8.6 (effective) |
| 51 years (left) | 37.0 | 35.9 | −1.1 | 33.2 | 34.5 | +1.3 | +2.4 (effective) |
| 45 years (right) | 52.5 | 49.9 | −2.6 | 45.4 | 45.3 | −0.1 | −2.5 (ineffective) |
| 28 years (right) | 42.1 | 44.9 | +2.8 | 43.9 | 44.1 | +0.2 | +2.6 (effective) |
| 33 years (left) | 35.4 | 35.9 | +0.5 | 46.7 | 48.0 | +1.3 | +0.8 (effective) |
| 30 years (left) | 44.0 | 43.1 | −0.9 | 38.3 | 40.9 | +2.6 | +3.5 (effective) |

Test Example 5 Arthrogryposis Improvement Test

This test was conducted by a physical therapist. The subject was a 78-years old female with spastic muscles in the lower limb and stroke hemiplegia. No improvement has been obtained by usual rehabilitation and the subject has been suffering from severe contracture and gait disorder. About 10 minutes after 1 g of the carbon dioxide external preparation of example 61 was applied to the lower leg, the dorsal flexion angle of the foot joint increased by 5°-10°, and the subject could walk easily. Therefore, arthrogryposis improvement effect of a carbon dioxide external preparation of the present invention was obvious.

Test Example 6 Pain Relief Test

This test was conducted by a physical therapist. The subject was a 58-years old female who has been suffering from de Quervain syndrome. Oral anti-inflammatory loxoprofen sodium had shown no effect on the pain of de Quervain syndrome. She had been suffering from sharp pain in the short rollical extensor muscle and the flexor hallucis abductor muscle of the radial aspect of the hand joint. About 10 minutes after 0.5 g of the carbon dioxide external preparation of example 58 was applied to the target area, the pain almost disappeared. Therefore, pain relief effect of a carbon dioxide external preparation of the present invention was obvious.

Test Example 7 Pain Relief Test

This test was conducted by a physical therapist. The subject was a 16-years old male baseball pitcher who has been suffering from pain in the musculus latissimus dorsi around the right scapula when he threw a ball. Diclofenac sodium ointment had shown no effect on the pain. About 10 minutes after 0.3 g of the carbon dioxide external preparation of example 64 was applied to the target area, the pain almost disappeared and the subject could throw a ball with full force. Therefore, pain relief effect of a carbon dioxide external preparation of the present invention was obvious.

It is obvious from the above results that a carbon dioxide external preparation of the present invention can provide an excellent carbon dioxide external preparation whose transdermal absorption amount of carbon dioxide is much, and carbon dioxide generation persists just by being applied to the skin or by additional water supply thereto.

Test Example 8 Ganglion Treatment Test

This test was conducted by an athletic trainer. The subject was a 20's male gymnast who had been suffering from ganglion with a diameter of 1 cm and 4 mm height on the front side of the left ankle. 0.1 g of a carbon dioxide external preparation of example 73 was applied to the ganglion and its surrounding skin once a day for a week. Then, the ganglion disappeared completely. Therefore, ganglion treatment effect of a carbon dioxide external preparation of the present invention was obvious.

Test Example 9 Pain And Knee Stiffness of Rheumatism Improvement Test

The subject was an 80's female whose pain and knee stiffness of rheumatism had not been improved by an oral anti-inflammatory loxoprofen sodium and the like. The subject did not wake at night for the knee pain and could walk easily after 2-3 days application of 0.1 g of the carbon dioxide external preparation of example 73 once a day to the knee skin. Therefore, pain and knee stiffness of rheumatism improvement effect of a carbon dioxide external preparation of the present invention was obvious.

Test Example 10 Pigmentation Improvement Test

The subject was a 40's female whose pubic hair was depilated at a clinic and she had got brown pigmentation in the depilated area. After a week of application of 0.1 g of the carbon dioxide external preparation of example 72 once a day to the pigmented area, no pigmentation was observed. The subject had been taking anti-inflammatory and the like for the same period, but it showed no effect, and pigmentation improvement effect of a carbon dioxide external preparation of the present invention was obvious.

INDUSTRIAL APPLICABILITY

A carbon dioxide external preparation of the present invention comprises a paste base agent, an alcohol, a carbonate, an acid and/or a substance that generates an acid by hydrolysis, and is useful because carbon dioxide specific actions and effects can be obtained just by being applied to the skin or just by being supplied with additional water thereto.

The invention claimed is:
1. A carbon dioxide external preparation, comprising:
   0.2-5 mass % of carboxyvinyl polymer and/or alkyl-modified carboxyvinyl polymer as a paste base agent;
   70-90 mass % of one or more alcohols selected from the group consisting of 1,3-butylene glycol, propylene glycol and glycerin;
   1-10 mass % of sodium bicarbonate as a carbonate; and
   1-10 mass % of malic acid and 1-10 mass % of sodium dihydrogen phosphate as an acid and/or a substance that generates an acid by hydrolysis.
2. The carbon dioxide external preparation according to claim 1, further comprising a water-soluble excipient.
3. The carbon dioxide external preparation according to claim 1, further comprising an exothermic agent.
4. The carbon dioxide external preparation according to claim 1, further comprising a desiccant.

* * * * *